US007314955B2

(12) United States Patent
Rajamahendra et al.

(10) Patent No.: US 7,314,955 B2
(45) Date of Patent: Jan. 1, 2008

(54) FORM OF N-(TRANS-4-ISOPROPYLCYCLO-HEXYLCARBONYL)-D-PHENYLALANINE

(75) Inventors: Shanmughasamy Rajamahendra, Tamil Nadu (IN); Chandrashekhar Aswathanarayanappa, Karnataka (IN); Tom Thomas Puthiaparampil, Karnataka (IN); Madhavan Sridharan, Karnataka (IN); Sambasivam Ganesh, Karnataka (IN)

(73) Assignee: Biocon Limited, Bangalore ( * ) Notice: Subject to any disclaimer, the term of this patent is extended or adjusted under 35 U.S.C. 154(b) by 395 days.

(21) Appl. No.: 10/508,364

(22) PCT Filed: Apr. 29, 2002

(86) PCT No.: PCT/IN02/00114

§ 371 (c)(1),
(2), (4) Date: Sep. 17, 2004

(87) PCT Pub. No.: WO03/093222

PCT Pub. Date: Nov. 13, 2003

(65) Prior Publication Data

US 2005/0165108 A1    Jul. 28, 2005

(51) Int. Cl.
*C07C 229/00*    (2006.01)
*A61K 31/195*    (2006.01)

(52) U.S. Cl. .................. 562/450; 562/444; 562/445; 514/563

(58) Field of Classification Search ............... 562/450, 562/444, 445; 514/563
See application file for complete search history.

(56) References Cited

U.S. PATENT DOCUMENTS

| 4,816,484 A | * | 3/1989 | Toyoshima et al. ......... 514/563 |
| 5,463,116 A | | 10/1995 | Sumikawa et al. |
| 5,488,150 A | | 1/1996 | Sumikawa et al. |

FOREIGN PATENT DOCUMENTS

| EP | 196 222 B1 | 10/1986 |
| WO | WO-03/093222 | 11/2003 |

OTHER PUBLICATIONS

Chemical Abstracts 136:159110; Li et al.: "A new crystal structure in nateglinide found by X-ray powder diffraction"; Yaowu Fenxi Zazhi (2001), 21(5), 342-44, Abstract.
Shinkai et al., "N-(Cyclohexylcarbonyl)-D-phenylalanines and Related Compounds. A New Class of Oral Hypoglycemic Agents, 2", *J. Med. Chem.*, 32(7): 1436-41, 1989.
International Search Report, PCT/IN02/00114, Sep. 5, 2002.
Written Opinion, PCT/IN02/00114, date of mailing Jun. 23, 2003.

* cited by examiner

*Primary Examiner*—Taylor Victor Oh
(74) *Attorney, Agent, or Firm*—Robin A. Weatherhead; Choate, Hall & Stewart LLP

(57) ABSTRACT

The present invention relates to a novel crystalline form of N-(trans-4-isopropylcyclohexylcarbonyl)-D-phenylalanine and methods for preparing the same.

16 Claims, 2 Drawing Sheets

FORM OF N-(TRANS-4-ISOPROPYLCYCLO-HEXYLCARBONYL)-D-PHENYLALANINE

PRIORITY CLAIM

Figure 1:
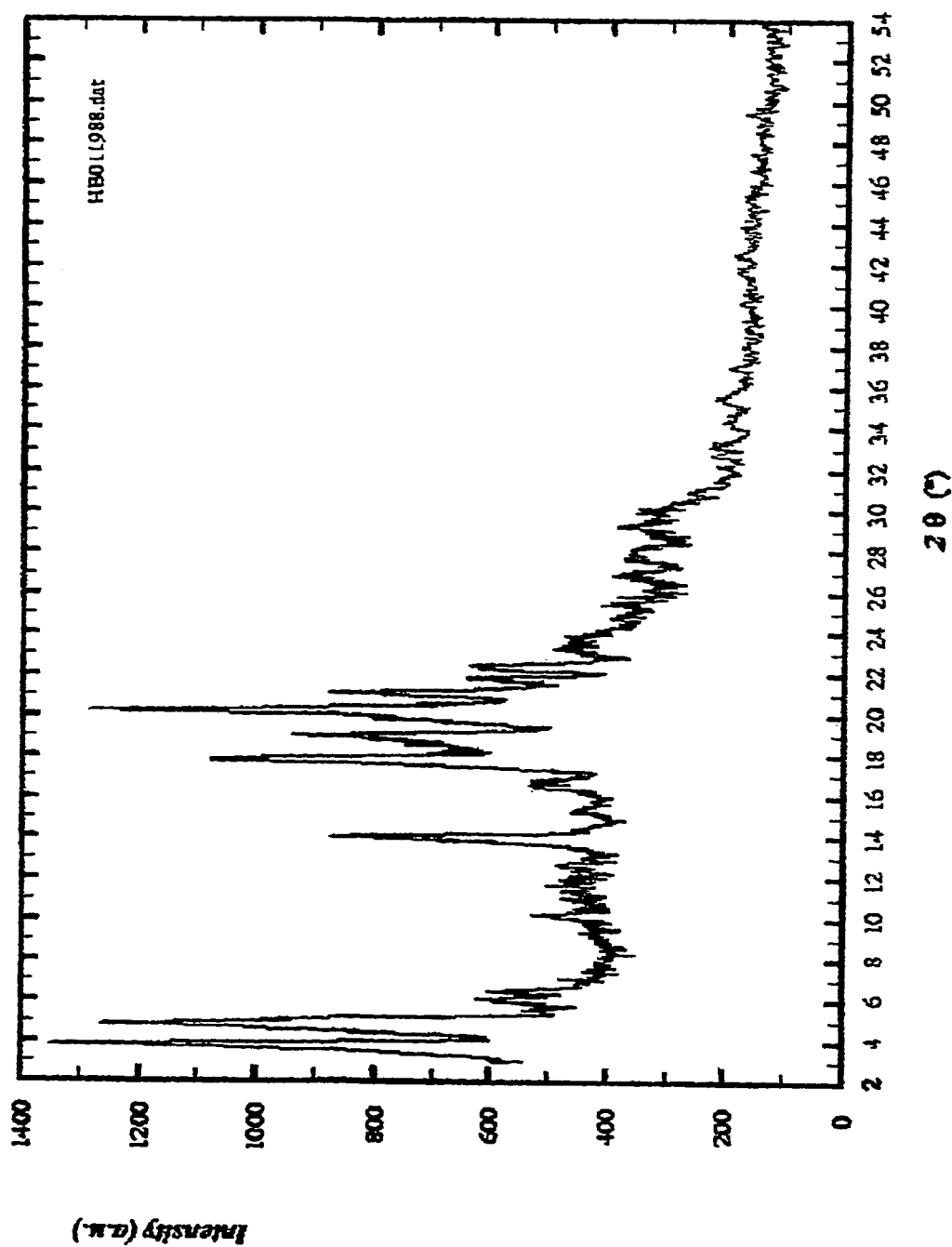

The present application claims the benefit under 35 U.S.C. §371 of International Application No.: PCT/IN02/00114 (published PCT application No. WO 03/093222), filed Apr. 29, 2002, the entirety of which is hereby incorporated herein by reference.

FIELD OF THE INVENTION

The present invention relates to a novel crystalline form of N-(trans-4-isopropylcyclohexylcarbonyl)-D-phenylalanine and methods for preparing the same.

BACKGROUND OF THE INVENTION

N-(trans-4-isopropylcyclohexylcarbonyl)-D-phenylalanine has therapeutic utility in depressing blood glucose levels in the management of type 2 diabetes mellitus.

N-(trans-4-isopropylcyclohexylcarbonyl)-D-phenylalanine is disclosed in Japanese Patent Application No. 63-54321 (equivalent to EP-A-196222 and U.S. Pat. No. 4,816,484). This Japanese application describes how the compound may be crystallized from aqueous methanol to yield crystals having a melting point of 129° C. to 130° C. These crystals are referred as "B-type". These B-type crystals suffer from problems of instability, especially when subjected to mechanical grinding.

J. Med. Chem. 32, 1436 (1989) describes the preparation of N-(cyclohexylcarbonyl)-D-phenylalanines and related compounds, including N-(trans-4-isopropylcyclohexylcarbonyl)-D-phenylalanine.

U.S. Pat. Nos. 5,463,116 and 5,488,150 describe the preparation of a novel crystalline form of N-(trans-4-isopropylcyclohexylcarbonyl)-D-phenylalanine designated "H-type". These patents also describe a method of treating form "B" crystals with appropriate solvent mixtures to obtain from "H" crystals and vice-versa. The H-type crystals have an enhanced stability over B type crystals.

Yaowu Fenxi Zazhi (2001), 21, 342 describes the "S" form of nateglinide as being different from form "B" and form "H".

SUMMARY OF THE INVENTION

According to a first aspect of the invention there is provided a process for the production of novel crystalline form "C" of N-(trans-4-isopropylcyclohexylcarbonyl)-D-phenylalanine by reacting D-phenylalanine methylester HCl with trans-4-isopropylcyclohexane carboxylic acid in presence of propane phosphonic acid anhydride or LiOH—Al$_2$O$_3$ in a halogenated hydrocarbon solvent such as dichloromethane or dichloroethane at a temperature between −10° C. to 90° C. followed by base hydrolysis.

Alternatively, the product can be obtained by reacting trans-4-isopropylcyclohexane carbonyl chloride with D-phenylalanine methyl ester HCl in a halogenated hydrocarbon solvent such as dichloromethane or dichloroethane in presence of a base such as triethylamine or pyridine at a temperature between −10° C. to 90° C. followed by base hydrolysis.

According to a still further aspect of the present invention, the new crystal from "C" of N-(trans-4-isopropylcyclohexylcarbonyl)-D-phenylalanine thus produced has at least one, and preferably all, of the following properties:

(a) a melting point in the range of 126° C. to 132° C.;
(b) a powder X-ray diffraction pattern comprising characteristic peaks at 14.0, 17.8, 19.0, 20.2 and 21.2±0.2 degrees measured at reflection angle 2θ; and
(c) an infrared absorption spectrum comprising absorption bands in the region of 1742, 1648, 1599, 1540 and 1191±2 cm$^{-1}$.

Yet another aspect of the invention includes form C N-(trans-4-isopropylcyclohexylcarbonyl)-D-phenylalanine for use in the preparation of a medicament for treating type 2 diabetes mellitus.

This invention also includes a pharmaceutical composition comprising a therapeutically effective amount of form C N-(trans-4-isopropylcyclohexylcarbonyl)-D-phenylalanine.

Another aspect of the invention relates to a method for treating a patient suffering from type 2 diabetes mellitus by administering to said patient a therapeutically effective amount of a pharmaceutical composition of form C N-(trans-4-isopropylcyclohexylcarbonyl)-D-phenylalanine.

BRIEF DESCRIPTION OF THE ACCOMPANYING DRAWINGS

Figure 2:
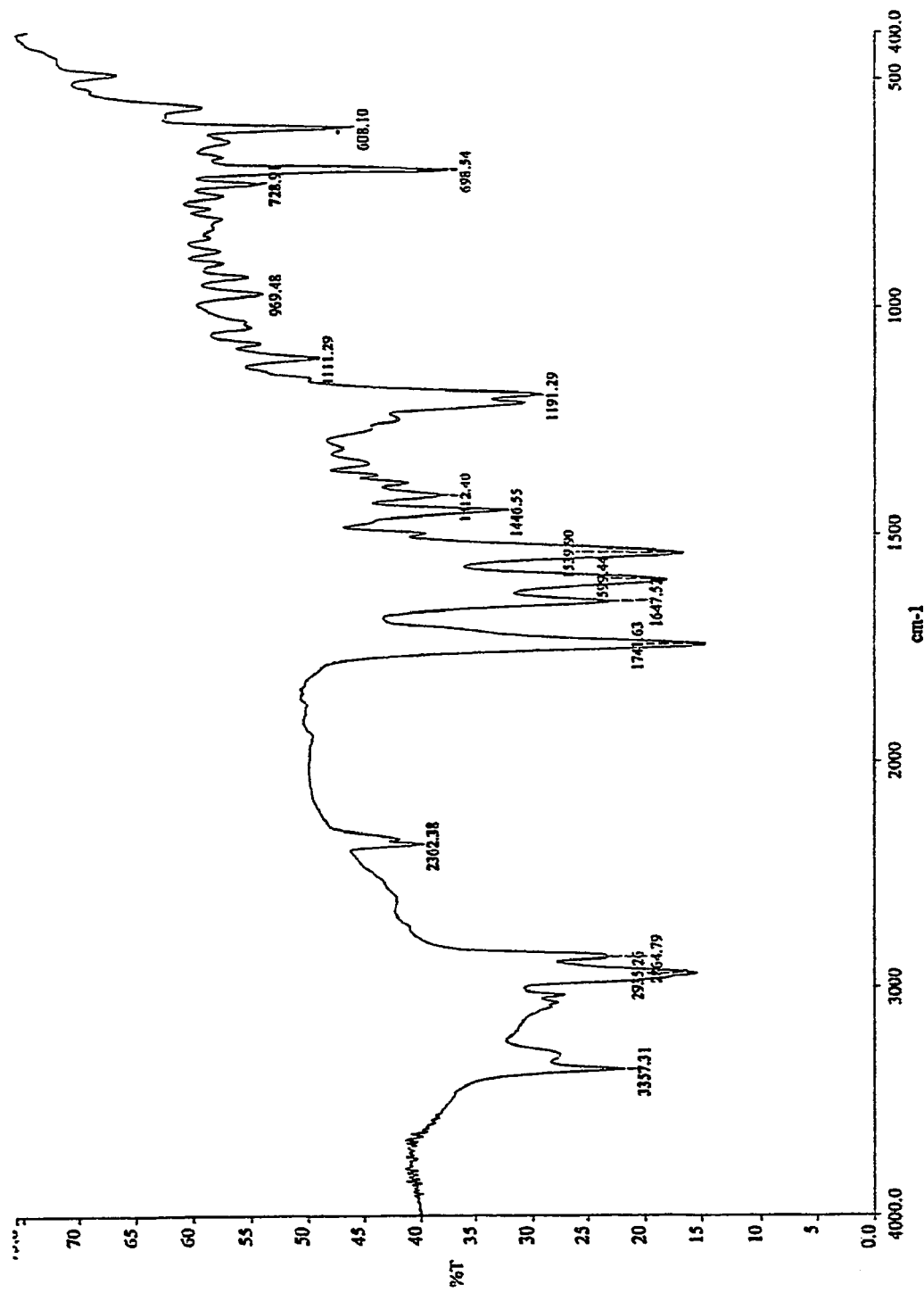

FIG. 1 shows a powder X-ray diffraction pattern of form C N-(trans-4-isopropylcyclohexylcarbonyl)-D-phenylalanine; and FIG. 2 shows an infra red absorption spectrum of form C of N-(trans-4-isopropylcyclohexylcarbonyl)-D-phenylalanine.

DETAILED DESCRIPTION OF CERTAIN EMBODIMENTS OF THE INVENTION

According to one embodiment, the process for preparing form C N-(trans-4-isopropylcyclohexylcarbonyl)-D-phenylalanine comprises the steps of:

(a) suspending N-(trans-4-isopropylcyclohexylcarbonyl)-D-phenylalanine methyl ester in water or a water miscible solvent;
(b) treating the suspension with a base;
(c) adding water followed by adjusting the pH to 1.0-4.0 using a mineral acid;
(d) extracting using ethyl acetate;
(e) concentrating the ethyl acetate extract;
(f) adding petroleum ether to the ethyl acetate concentrate; and
(g) filtering and drying the resulting precipitate to get form C N-(trans-4-isopropylcyclohexylcarbonyl)-D-phenylalanine.

In certain embodiments, the water miscible solvent in step (a) above is selected from methanol, ethanol, isopropanol, or a mixture thereof. In other embodiments, the water miscible solvent in step (a) above is selected from methanol.

In other embodiments, the base in step (b) above is selected from potassium carbonate, sodium carbonate, sodium hydroxide, potassium hydroxide, lithium hydroxide or a mixture thereof. In still other embodiments, the base in step (b) above is potassium carbonate.

In certain embodiments, the precipitate obtained in step (g) above is suspended in water before filtration and drying to get form C N-(trans-4-isopropylcyclohexylcarbonyl)-D-phenylalanine.

In certain embodiments, N-(trans-4-isopropylcyclohexylcarbonyl)-D-phenylalanine methyl ester is prepared by:

(i) reacting D-phenylalanine methyl ester hydrochloride with trans-4-isopropylcyclohexane carboxylic acid in a halogenated hydrocarbon solvent;
(ii) filtering the reaction mixture; and
(iii) concentrating the resulting filtrate to get N-(trans-4-isopropylcyclohexylcarbonyl)-D-phenylalanine methyl ester.

In other embodiments, step (i) in the above process for the preparation of N-(trans-4-isopropylcyclohexylcarbonyl)-D-phenylalanine methyl ester is carried out in the presence of propane phosphonic acid anhydride, LiOH adsorbed onto aluminum oxide or triethylamine.

In still other embodiments, an alternate method for producing N-(trans-4-isopropylcyclohexylcarbonyl)-D-phenylalanine methyl ester comprises the steps of:
(i) reacting D-phenylalanine methyl ester hydrochloride with trans-4-isopropylcyclohexane carbonyl chloride in a halogenated hydrocarbon solvent and in the presence of a base;
(ii) filtering the reaction mixture; and
(iii) concentrating the resulting filtrate to get N-(trans-4-isopropylcyclohexylcarbonyl)-D-phenylalanine methyl ester.

In certain embodiments, the halogenated hydrocarbon solvent is selected from dichloromethane or dichloroethane.

In other embodiments, the base is selected from triethylamine or pyridine.

In still other embodiments, the reaction temperature is −10° to 90° C.

Embodiments of the invention are illustrated below by way of the following examples, which are not to be considered as limiting.

EXAMPLE 1

N-(trans-4-isopropylcyclohexylcarbonyl)-D-phenylalanine methyl ester (Method A): D-Phenylalanine methyl ester hydrochloride (10 g, 0.046 mol) was suspended in a solution of triethylamine (33 mL) in dichloromethane (50 mL). The mixture was cooled to 0-5° C. and trans-4-isopropylcyclohexane carboxylic acid (7.9 g, 0.046 mol) was added. A solution of propane phosphonic acid anhydride (46.4 mL, 0.046 mol) in ethyl acetate was added dropwise over a period of 30 minutes, maintaining the temperature at 0-5°. The resulting mixture was stirred for 14 hours at ambient temperature. The reaction mixture was washed with 1.5 N HCl, 5% sodium bicarbonate solution and brine. The organic layer was concentrated to yield 12.5 g of N-(trans-4-isopropylcyclohexylcarbonyl)-D-phenylalanine methyl ester.

EXAMPLE 2

N-(trans-4-isopropylcyclohexylcarbonyl)-D-phenylalanine methyl ester (Method B): D-Phenylalanine methyl ester hydrochloride (20 g, 0.092 mol) was suspended in a solution of triethylamine (66 mL) in dichloroethane (100 mL) and the mixture was stirred for 1 hour at room temperature. The organic layer was separated after washing with water and dried over anhydrous sodium sulphate. Trans-4-isopropylcyclohexane carboxylic acid (15.8 g, 0.092 mol) was added to the organic layer followed by LiOH—Al$_2$O$_3$ (5.5 g of LiOH adsorbed on 40.5 g aluminum oxide) and the resulting mixture heated at for 24 hours. The reaction mixture was filtered through a celite bed and washed with 1.5 N HCl, 5% sodium bicarbonate solution and brine. The organic layer was concentrated to yield 15.5 g of N-(trans-4-isopropylcyclohexylcarbonyl)-D-phenylalanine methyl ester.

EXAMPLE 3

N-(trans-4-isopropylcyclohexylcarbonyl)-D-phenylalanine methyl ester (Method C): D-Phenylalanine methyl ester hydrochloride (26 g, 0.12 mol) was suspended in a solution of triethylamine (85 mL) in dichloromethane (125 mL) and the mixture was cooled to 0-5° C. A solution of trans-4-isopropylcyclohexane carbonyl chloride (25 g, 0.13 mol) in dichloromethane (75 mL) was added dropwise over a period of 10 minutes while maintaining the temperature at 0-5° C. The resulting mixture was stirred for 12 hours at ambient temperature then washed with 1.5 N HCl, 5% sodium bicarbonate solution and brine. The organic layer was concentrated to yield 38 g of N-(trans-4-isopropylcyclohexylcarbonyl)-D-phenylalanine methyl ester.

EXAMPLE 4

Form C N-(trans-4-isopropylcyclohexylcarbonyl)-D-phenylalanine: To suspension of N-(trans-4-isopropylcyclohexylcarbonyl)-D-phenylalanine methyl ester (38 g, 0.11 mol) in methanol (600 mL) was added a solution of potassium carbonate (80 g, 0.57 mol) in water (400 mL) and the reaction mixture stirred for 12 hours at ambient temperature. Water (1500 mL) was added and the pH was adjusted to 2.0 by adding 6N HCl. The mixture was extracted with ethyl acetate (3×400 mL) and the combined extracts were washed with brine. The organic layer was concentrated to about 150 mL then petroleum ether (300 mL) was added. The product was filtered and suspended in water (600 mL) and stirred for 12 hours at ambient temperature. The slurry was filtered and dried to yield 35 g of the title compound. The compound showed a sharp melting point of 128-129° C. X-ray diffraction pattern and infra red absorption spectrum of the final compound were recorded and identified as form C crystals of N-(trans-4-isopropylcyclohexylcarbonyl)-D-phenylalanine.

We claim:
1. Crystalline form "C" N-(trans-4-isopropylcyclohexylcarbonyl)-D-phenylalanine having at least two of the following properties:
   (a) a melting point in the range of 126° to 132° C.;
   (b) a powder X-ray diffraction pattern comprising characteristic peaks at 14.0, 17.8, 19.0, 20.2 and 21.2+0.2 degrees measured at reflection angle 2θ; and
   (c) an infrared absorption spectrum comprising absorption bands in the region of 1742, 1648, 1599, 1540 and 1191+2 cm$^{-1}$.
2. Crystalline form "C" N-(trans-4-isopropylcyclohexylcarbonyl)-D-phenylalanine having at least one of the following properties:
   (a) a powder X-ray diffraction pattern in accordance with FIG. 1; and
   (b) an infrared absorption spectrum in accordance with FIG. 2.
3. A process for preparing form "C" N-(trans-4-isopropylcyclohexylcarbonyl)-D-phenylalanine comprising the steps of:
   (a) suspending N-(trans-4-isopropylcyclohexylcarbonyl)-D-phenylalanine methyl ester in water or a water miscible solvent;
   (b) treating the suspension with a base;
   (c) adding water followed by adjusting the pH to 1.0-4.0 using a mineral acid;
   (d) extracting using ethyl acetate;
   (e) concentrating the ethyl acetate extract;

(f) adding petroleum ether to the ethyl acetate concentrate; and (g) filtering and drying the resulting precipitate to get form "C" N-(trans-4-isopropylcyclohexylcarbonyl)-D-phenylalanine.

4. The process of claim 3, wherein the water miscible solvent in step (a) is selected from the group consisting of methanol, ethanol, isopropanol, and a mixture thereof.

5. The process of claim 4, wherein the water miscible solvent in step (a) is methanol.

6. The process of claim 3, wherein the base in step (b) is selected from the group consisting of potassium carbonate, sodium carbonate, sodium hydroxide, potassium hydroxide, lithium hydroxide and a mixture thereof.

7. The process of claim 6, wherein the base in step (b) is potassium carbonate.

8. The process of any one of claims 3-7, further comprising the step of suspending the precipitate obtained in step (g) in water before filtering and drying to get form "C" N-(trans-4-isopropylcyclohexylcarbonyl)-D-phenylalanine.

9. The process of claim 3, wherein the N-(trans-4-isopropylcyclohexylcarbonyl)-D-phenylalanine methyl ester of step (a) is prepared by:
(i) reacting D-phenylalanine methyl ester hydrocholoride with trans-4-isopropylcyclohexane carboxylic acid in a halogenated hydrocarbon;
(ii) filtering the reaction mixture; and
(iii) concentrating the resulting filtrate to get N-(trans-4-isopropylcyclohexylcarbonyl)-D-phenylalanine methyl ester.

10. The process of claim 9, wherein said halogenated hydrocarbon solvent is selected from the group consisting of dichloromethane and dichloroethane.

11. The process of claim 9, wherein step (i) is carried out in the presence of propane phosphonic acid anhydride, LiOH adsorbed onto aluminum oxide or triethylamine.

12. The process of claim 3, wherein the N-(trans-4-isopropylcyclohexylcarbonyl)-D-phenylalanine methyl ester of step (a) is prepared by:
(i) reacting D-phenylalanine methyl ester hydrochloride with trans-4-isopropylcyclohexane carbonyl chloride in a halogenated hydrocarbon solvent and in the presence of a base;
(ii) filtering the reaction mixture; and
(iii) concentrating the resulting filtrate to get N-(trans-4-isopropylcyclohexylcarbonyl)-D-phenylalanine methyl ester.

13. The process of claim 12, wherein said halogenated hydrocarbon solvent is selected from the group consisting of dichloromethane and dichloroethane.

14. The process of claim 12, wherein said base is selected from the group consisting of triethylamine and pyridine.

15. The process of either of claims 9 or 12, wherein the reaction temperature is −10° to 90° C.

16. Crystalline form "C" N-(trans-4-isopropylcyclohexylcarbonyl)-D-phenylalanine having at least two of the following properties:
(a) a melting point in the range of 126° to 132° C.;
(b) a powder X-ray diffraction pattern comprising characteristic peaks at 14.0, 17.8, 19.0, 20.2 and 21.2+0.2 degrees measured at reflection angle 2θ; and
(c) an infrared absorption spectrum comprising absorption bands in the region of 1742, 1648, 1599, 1540 and 1191+2 $cm^{-1}$;

obtained by the process of:
(i) suspending N-(trans-4-isopropylcyclohexylcarbonyl)-D-phenylalanine methyl ester in water or a water miscible solvent;
(ii) treating the suspension with a base;
(iii) adding water followed by adjusting the pH to 1.0-4.0 using a mineral acid;
(iv) extracting using ethyl acetate;
(v) concentrating the ethyl acetate extract;
(vi) adding petroleum ether to the ethyl acetate concentrate; and
(vii) filtering and drying the resulting precipitate to get form "C" N-(trans-4-isopropylcyclohexylcarbonyl)-D-phenylalanine.

* * * * *